(12) United States Patent
Neubardt

(10) Patent No.: US 10,363,143 B2
(45) Date of Patent: Jul. 30, 2019

(54) HARVESTING BONE GRAFT MATERIAL FOR USE IN SPINAL AND OTHER BONE FUSION SURGERIES

(71) Applicant: Seth L. Neubardt, Rye, NY (US)

(72) Inventor: Seth L. Neubardt, Rye, NY (US)

( * ) Notice: Subject to any disclaimer, the term of this patent is extended or adjusted under 35 U.S.C. 154(b) by 323 days.

(21) Appl. No.: 15/399,198

(22) Filed: Jan. 5, 2017

(65) Prior Publication Data
US 2017/0156888 A1    Jun. 8, 2017

Related U.S. Application Data

(63) Continuation-in-part of application No. 14/688,544, filed on Apr. 16, 2015, now Pat. No. 9,636,232.

(60) Provisional application No. 62/274,961, filed on Jan. 5, 2016.

(51) Int. Cl.
| | |
|---|---|
| *A61B 17/16* | (2006.01) |
| *A61F 2/44* | (2006.01) |
| *A61F 2/46* | (2006.01) |
| *A61B 17/32* | (2006.01) |
| *A61F 2/30* | (2006.01) |
| *A61B 17/00* | (2006.01) |
| *A61B 17/3207* | (2006.01) |

(52) U.S. Cl.
CPC ........ *A61F 2/4455* (2013.01); *A61B 17/1635* (2013.01); *A61B 17/1671* (2013.01); *A61B 17/320068* (2013.01); *A61F 2/442* (2013.01); *A61F 2/4601* (2013.01); *A61F 2/4611* (2013.01); *A61F 2/4644* (2013.01); *A61B 17/32002* (2013.01); *A61B 2017/00969* (2013.01); *A61B 2017/320072* (2013.01); *A61B 2017/320733* (2013.01); *A61F 2002/30589* (2013.01); *A61F 2002/445* (2013.01); *A61F 2002/4475* (2013.01); *A61F 2002/4681* (2013.01)

(58) Field of Classification Search
CPC .................................................. A61B 17/1635
See application file for complete search history.

(56) References Cited

U.S. PATENT DOCUMENTS

| | | | |
|---|---|---|---|
| D625,820 S | 10/2010 | Calverley et al. | |
| D629,104 S | 12/2010 | Calverley et al. | |
| 9,042,960 B2 | 5/2015 | Neubardt | |
| 2006/0195107 A1 | 8/2006 | Jones et al. | |
| 2007/0055260 A1* | 3/2007 | Cragg | A61B 17/1631 606/79 |

(Continued)

*Primary Examiner* — Samuel S Hanna
(74) *Attorney, Agent, or Firm* — Leo Zucker

(57) ABSTRACT

A cage or spacer device for harvesting bone graft material for use in bone fusion surgery, e.g., spinal fusion. The device is inserted between facing surfaces of the bones to be fused, and a chamber is formed in the device for containing a slurry of morselized bone and blood to be effused from the bones. In one embodiment, a bone cutter assembly including a cannula having a bend at a distal end is inserted in the chamber for operation. A wire having a cutting tip is passed inside the cannula so that the tip projects a determined distance from the distal end of the cannula. Accordingly, the cutting tip strikes and cuts grooves in the facing surfaces of the bones when the cannula is rotationally driven about its axis. The mentioned slurry effuses from the grooved surfaces and remains in the chamber to promote a solid and healthy fusion.

3 Claims, 19 Drawing Sheets

(56) References Cited

U.S. PATENT DOCUMENTS

| | | |
|---|---|---|
| 2009/0054994 A1 | 2/2009 | Rogan et al. |
| 2011/0035007 A1 | 2/2011 | Patel et al. |
| 2015/0351777 A1* | 12/2015 | Lizardi .............. A61B 17/1622 606/80 |
| 2016/0113780 A1 | 4/2016 | Neubardt |

* cited by examiner

HARVESTING BONE GRAFT MATERIAL FOR USE IN SPINAL AND OTHER BONE FUSION SURGERIES

CROSS REFERENCE TO RELATED APPLICATIONS

This application is a continuation-in-part (CIP) of my co-pending U.S. patent application Ser. No. 14/688,544 filed Apr. 16, 2015. The present application also claims priority under 35 U.S.C. § 119(e) of U.S. Provisional Patent Application No. 62/274,961 filed Jan. 5, 2016, the entire contents of which are incorporated by reference.

BACKGROUND OF THE INVENTION

Field of the Invention

The present invention relates to a system and devices for harvesting bone graft material for use in bone fusion surgery, including but not limited to fusions of the spine.

Discussion of the Known Art

An object of spinal fusion surgery is to join vertebrae solidly to one another at an affected level of a patient's spine, by inducing growth of bone tissue that is deposited between the vertebrae during the surgery. When fully grown, the deposited tissue fuses the vertebrae solidly and permanently. The procedure is long known to reduce or eliminate severe back pain when, for example, an intervertebral disc is damaged or becomes ineffective. See, e.g., U.S. Pat. No. 9,042,960 (May 26, 2015) titled Determining and Placing Spinal Implants or Prostheses, which is incorporated by reference.

In a typical fusion procedure, a disc space is cleaned between each pair of vertebrae to be fused, and bone or a bone graft material is deposited in the space in such a way that the material will grow and achieve a healthy fusion. Among available bone graft materials, graft harvested directly from the patient's own bone tissue (autograft) or from a donor, ceramics, bone morphogenic proteins, and/or stem cell based grafts are frequently used. Of these, autograft obtained from the patient's iliac crest or pelvic area is known to work best to achieve a successful fusion.

Using the patient's own bone tissue as graft material works well to form a confluence of the material with the vertebral bones to be fused. It is also known that (a) the more autograft material used, the greater the likelihood of achieving a successful fusion, and (b) a solid piece of autograft material works better than smaller chips to promote fusion. Basic principles of orthopaedic surgery suggest that an optimum fusion results when a solid piece of bone is inserted to span the entire intervertebral disc space, and when opposite ends of the piece enter or penetrate the vertebral end plates facing the space.

U.S. Pat. No. 7,201,775 (Apr. 10, 2007) discloses a procedure that includes implanting a hollow cylindrical stabilizing device (see FIGS. 7 & 8 of the patent) between the end plates the vertebrae to be fused, and rotating the device so it gouges and shears off portions of the end plates which are then forced inside the device. The Device has openings formed so that when oriented as in FIG. 11C of the patent, the sheared bone portions are exposed to the vertebrae through the openings in order to promote fusion. The procedure involves a risk of crushing the end plates and thereby destroying the integrity of the remaining vertebral bone, however. That is, after the end plates are sheared by the device, one or both vertebrae may become prone to fracture and compress into the spinal canal. Also, the device does not work to translocate or displace a solid piece of bone from one of the vertebra so that an end of the piece enters the body of the other vertebra.

U.S. Pat. No. 8,328,870 (Dec. 11, 2012) describes an interbody fixation system including a cage having a number of blades mounted inside the cage. When the blades are turned by not more than 45 degrees as shown in FIGS. 2 and 6C of the patent, the blades bite into the end plates of the opposed vertebrae and fix the position of the cage on and between the end plates. See also, U.S. Pat. No. 7,618,423 (Nov. 17, 2009) which relates to a system for performing spinal fusion including a graft holder assembly, a locking assembly, and a pair of bone graft implants that are introduced into a disc space to effect fusion; U.S. Pat. No. 8,353,912 (Jan. 15, 2013) disclosing an ultrasonic cleaning device for leveling the surfaces of vertebral end plates after the disc space between them is cleaned and before graft material is deposited in the space; and U.S. Pat. No. 8,343,178 (Jan. 1, 2013) describing an ultrasonic saw blade for cutting hard bone without damaging adjacent soft tissue. All relevant portions of the mentioned patents are incorporated by reference.

Notwithstanding known meticulous procedures for obtaining and using autograft material from a patient during surgery, there is no guarantee that a reliable and strong fusion will always be obtained, and that a so-called "non-union" will be avoided. A need therefore exists for a system or a device for obtaining autograft material from a patient during a bone fusion surgery, and for depositing the material between the bones to be fused so that (a) the material spans the space between the bones and also penetrates the bones, and (b) the material grows rapidly to obtain a healthy, strong, and permanent fusion of the bones.

SUMMARY OF THE INVENTION

According to the invention, a cage device for harvesting bone graft material for use in fusion surgery, includes a housing constructed and arranged for insertion to a desired position in a space between two bones to be fused. The housing has a chamber that opens at top and bottom ends of the device facing the bones, and the chamber is arranged to contain a slurry of morselized bone and blood when effused by the bones.

The device also includes a bone cutter assembly having an elongated cannula, and a bend is formed at a distal end or tip of the cannula. A wire with a cutting tip is inserted through the cannula so that the cutting tip extends a desired distance from the distal end of the cannula to contact the bones, when the end of the cannula is inserted in the housing chamber. The cutting tip grooves the bones when the cannula is rotated about its axis by an outside drive, so that a slurry of morselized bone and blood effuses from the grooved bones and enters the housing chamber to promote fusion of the bones.

According to another aspect of the invention, cage or spacer device for harvesting bone graft material for use in fusion surgery, includes a rectangular body having an outer wall that defines a chamber through the body. The outer wall has opposed first and second short sides and opposed first and second long sides, and an opening the first short side of the wall is formed to engage a tool for inserting the device between two bones to be fused.

A shaft extends inside the chamber between the first and second long sides of the outer wall, wherein the shaft is supported for rotation about its axis, and a gearbox is mounted on the shaft. A first gear is fixed coaxially on the shaft inside the gearbox, and a side of the gearbox is open for access to the first gear.

A sleeve is fixed at one end in axial alignment with the opening in the first short side of the outer wall, and the opposite end of the sleeve is fixed to the side of the gearbox open for access to the first gear. Accordingly, (i) a drive having a second gear at a distal end of the drive is insertable through the opening in the first short side of the outer wall until the second gear at the end of the drive engages the first gear on the shaft, and (ii) the shaft is driven to rotate when the drive is rotationally driven by a component outside the device.

One or more hubs are fixed coaxially on the shaft at positions outside the gearbox, and one or more wires each having a cutting tip at a distal end of the wire is fixed to each hub. The wires are of a sufficient length to extend above and below the body of the cage device to cut bones between which the device is inserted when the shaft is driven to rotate.

For a better understanding of the invention, reference is made to the following description taken in conjunction with the accompanying drawing and the appended claims.

BRIEF DESCRIPTION OF THE DRAWING FIGURES

Figure 1:
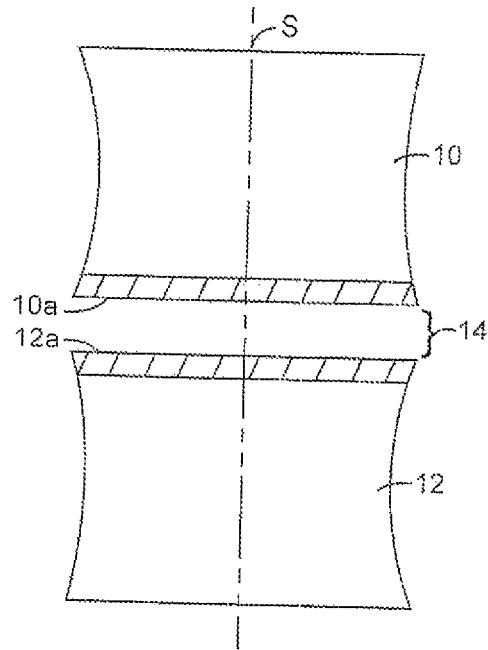
FIG. 1 illustrates two adjacent spinal vertebrae to be fused to one another, according to a first embodiment of the invention.
Figure 6:
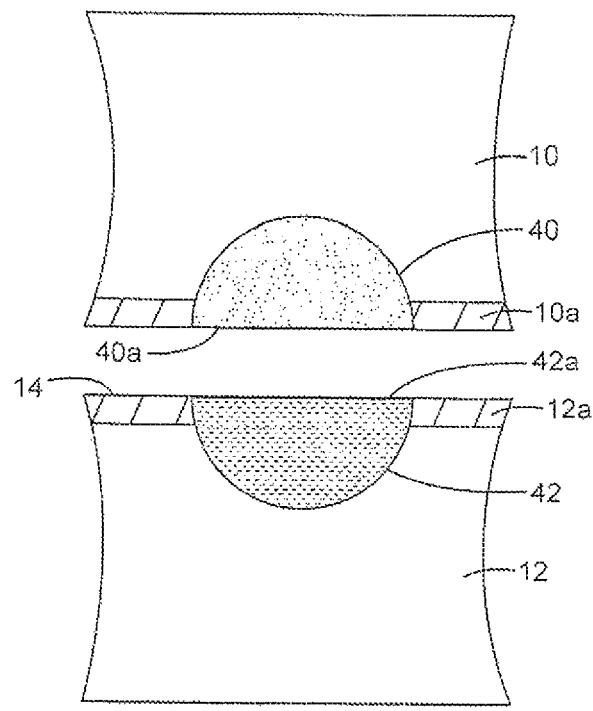
FIG. 6 illustrates two bone segments that were cut and formed inside the vertebrae by the tool blade.
Figure 10:
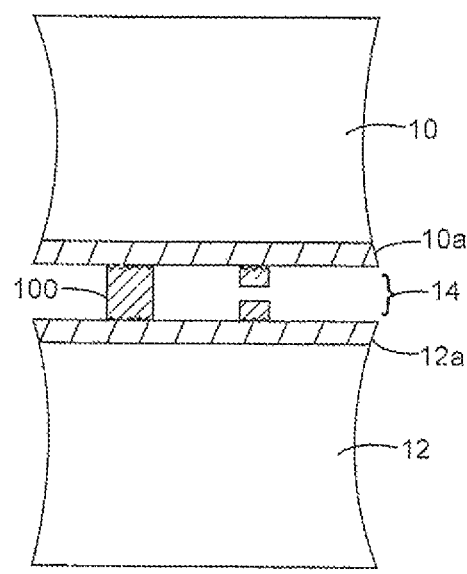
Figure 8:
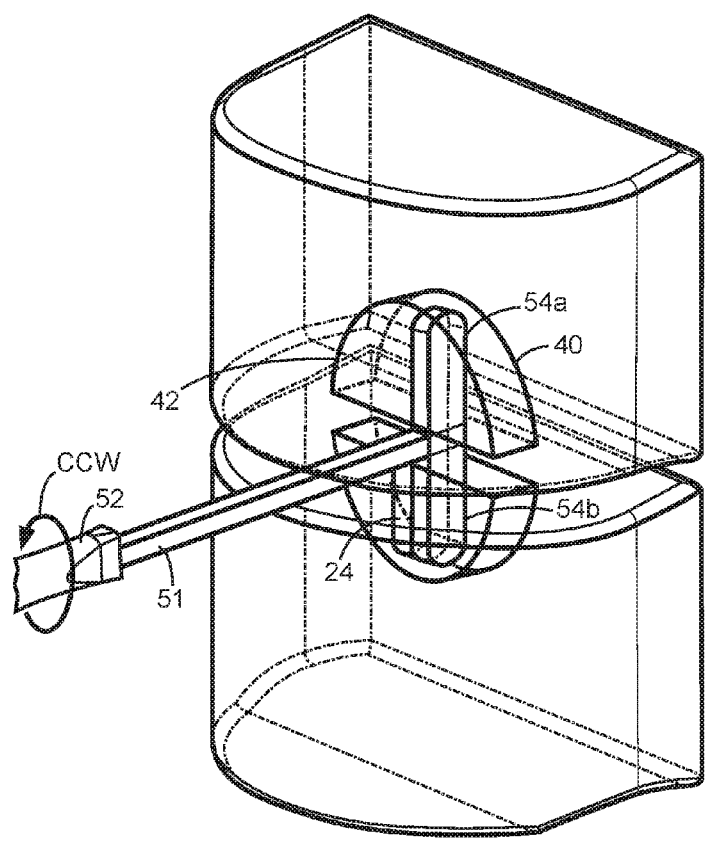
FIG. 8 is a view similar to FIG. 7, showing the paddle inserted in the disc space and after being turned 90 degrees from the position in FIG. 7.
Figure 9:
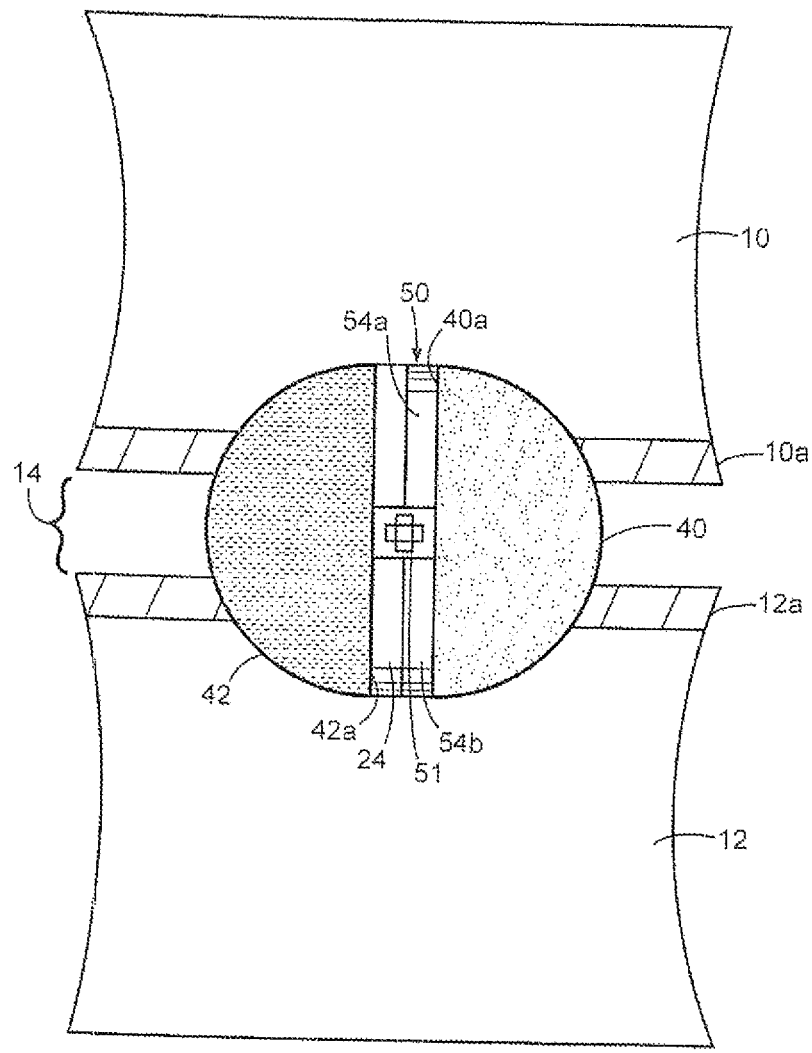
Figure 11:
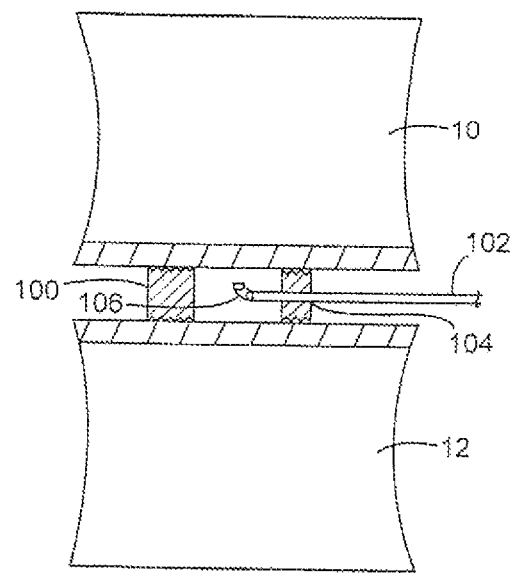
Figure 12:
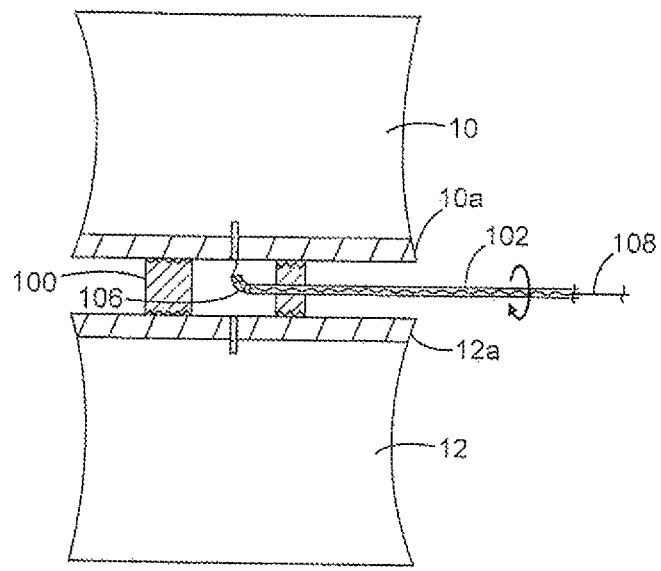
Figure 13:
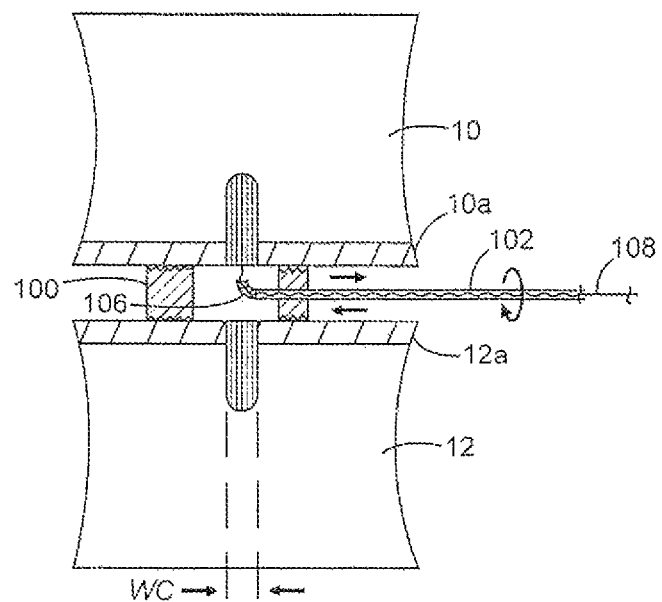
Figure 14:
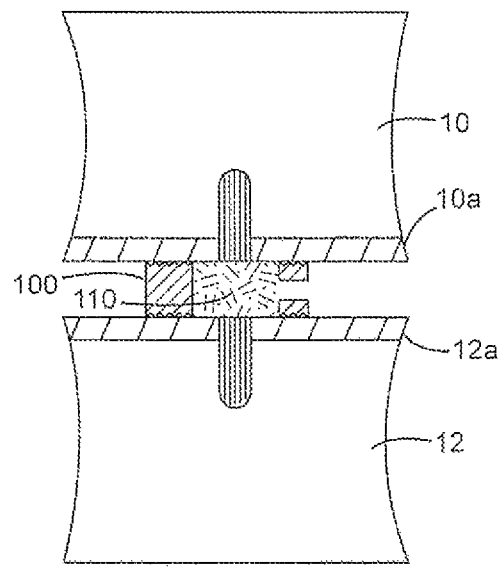
Figure 15:
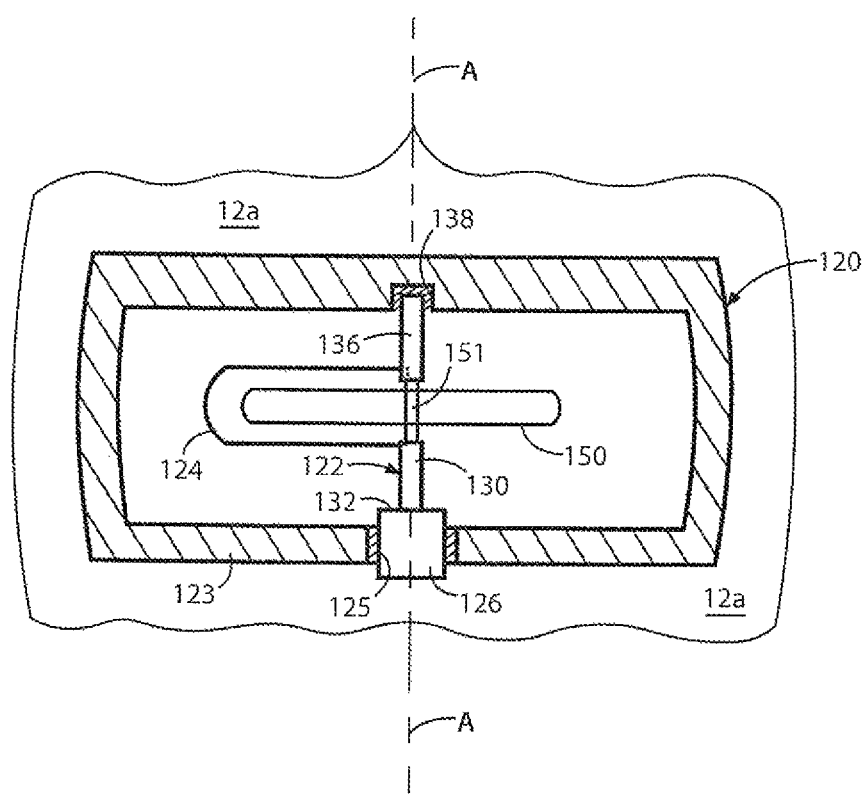
Figure 16:
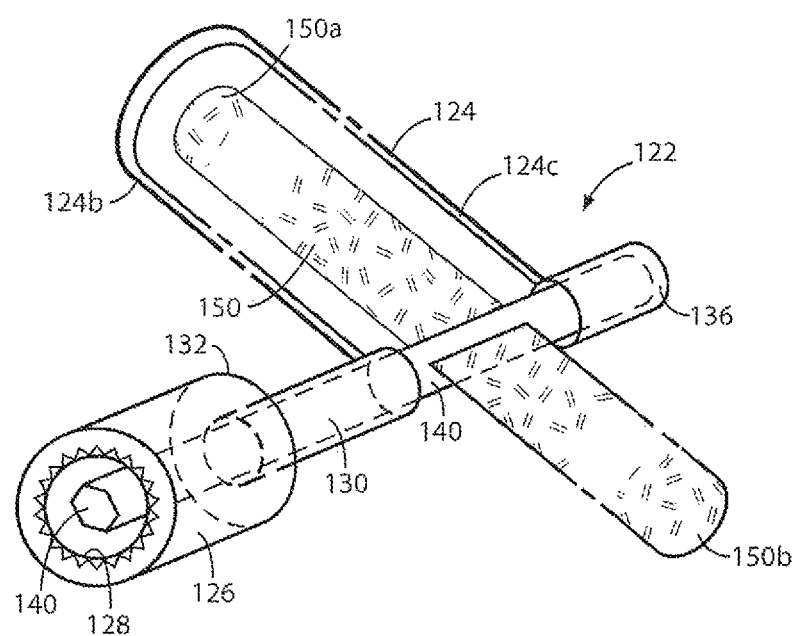
Figure 17:
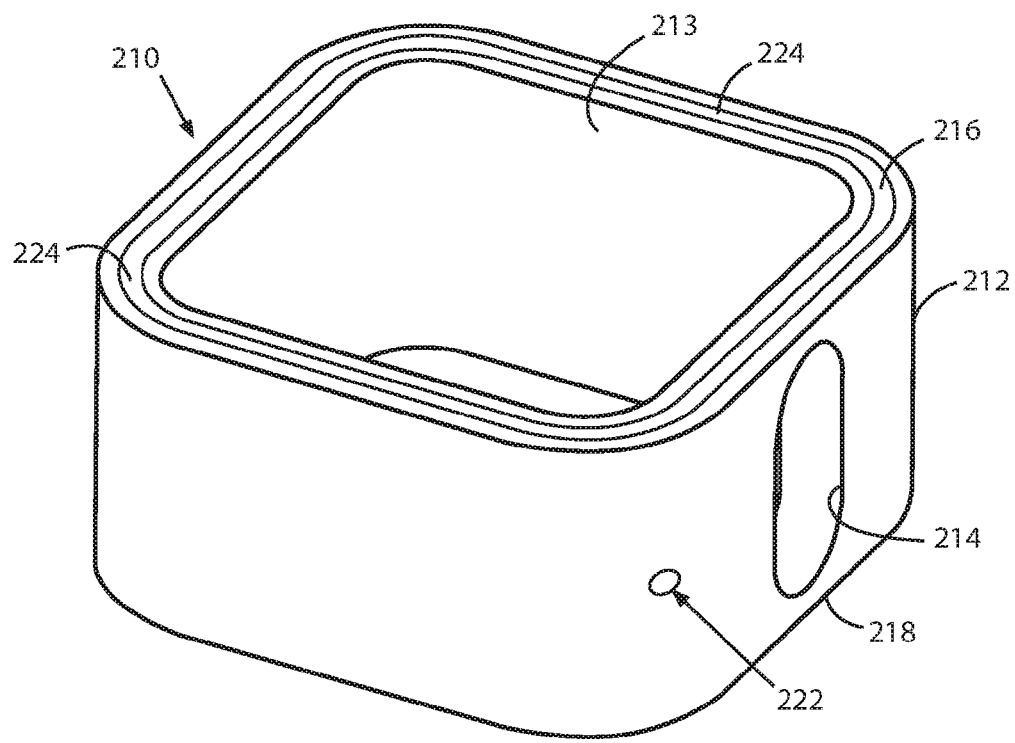
Figure 18:
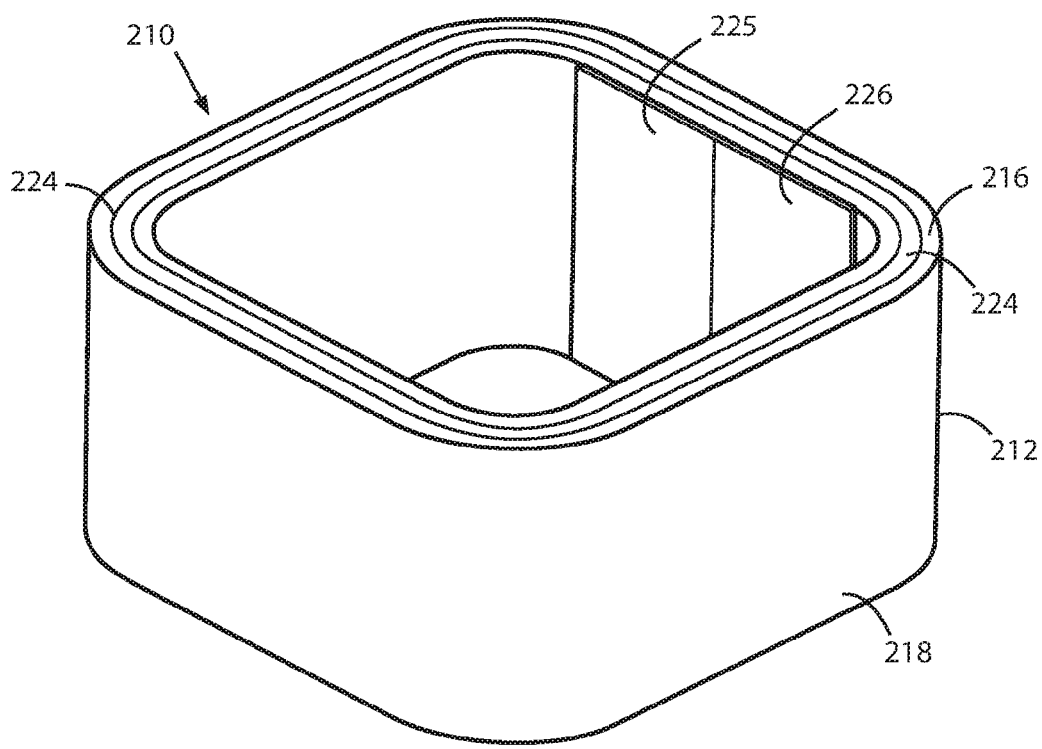
Figure 19:
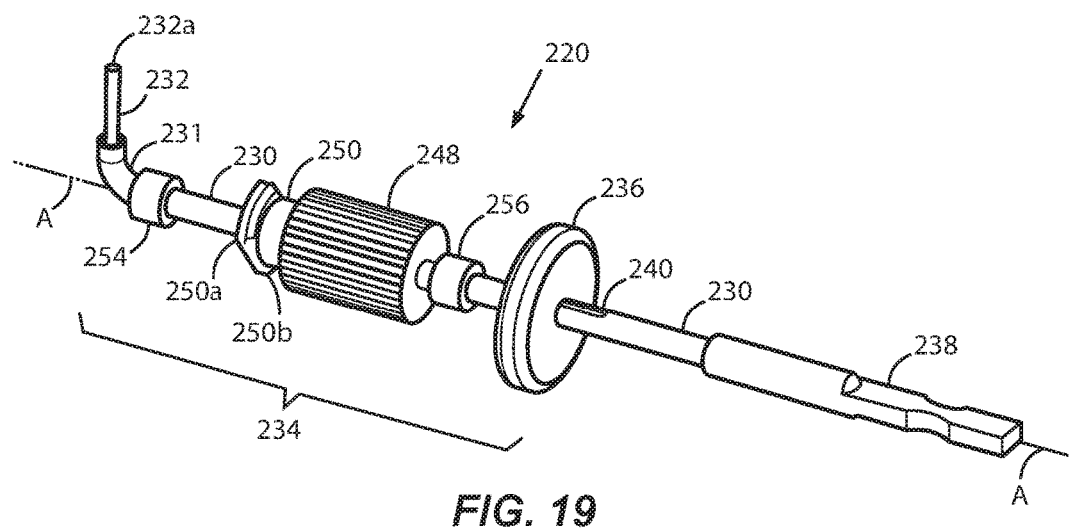
Figure 20:
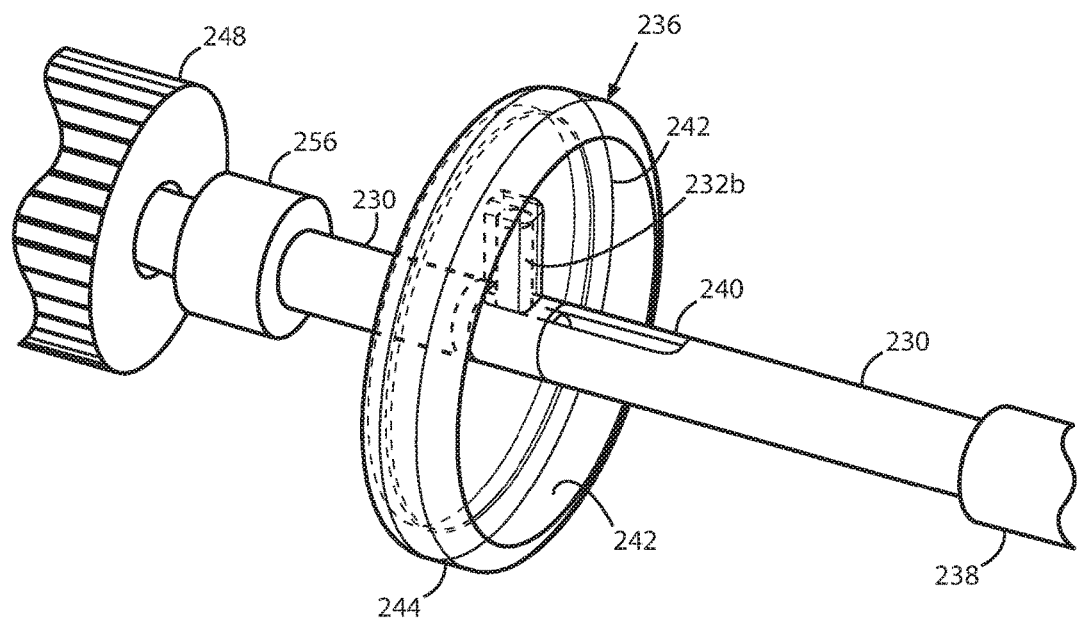
Figure 21:
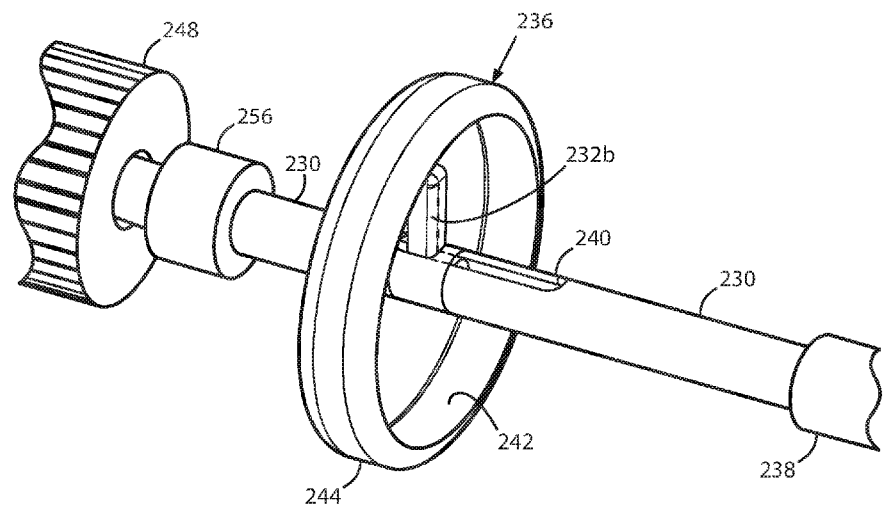
Figure 22:
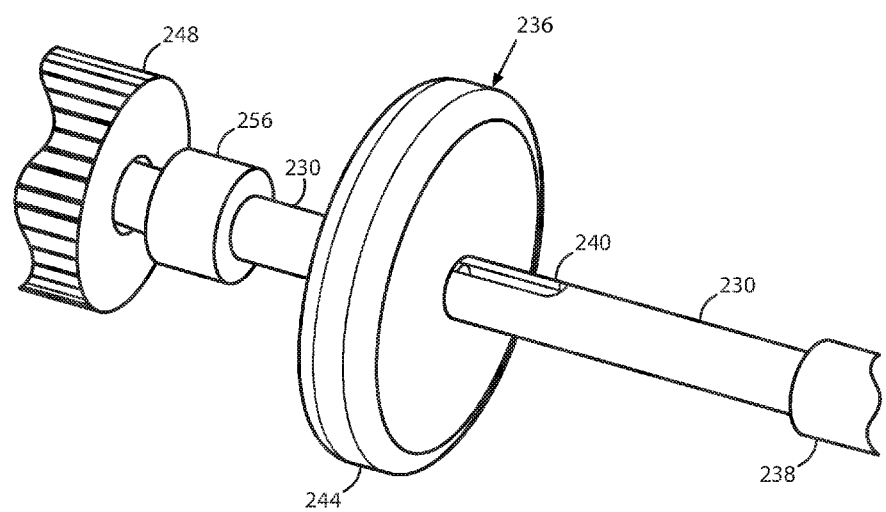
Figure 23:
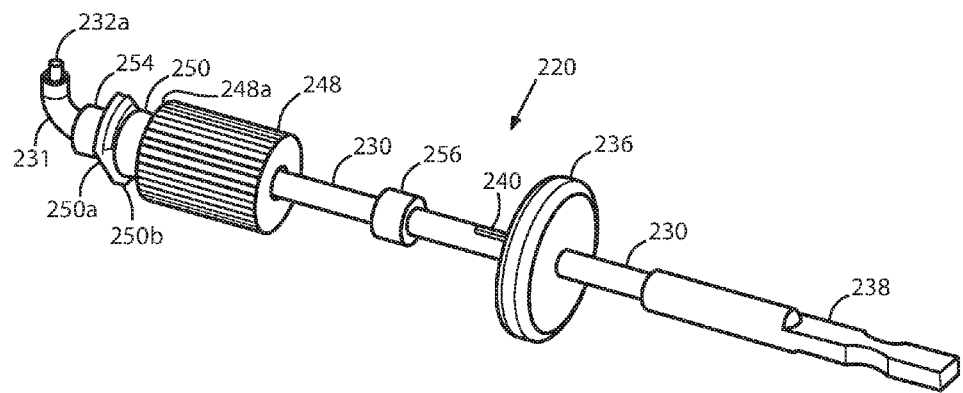
Figure 24:
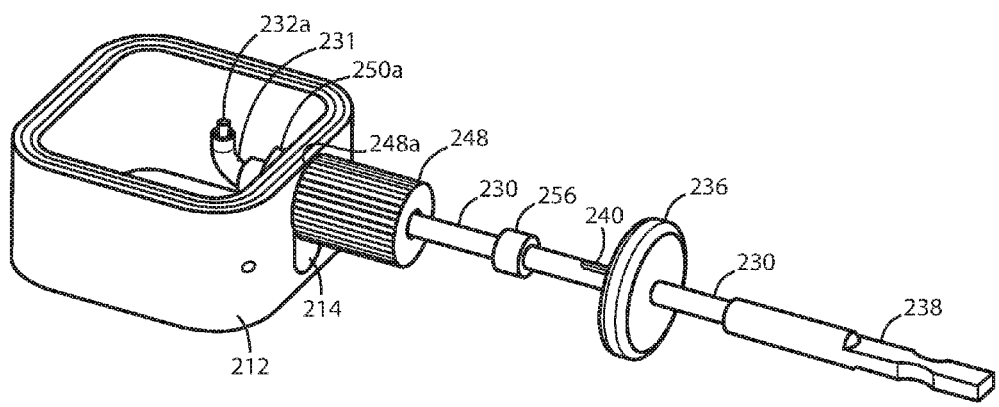
Figure 25:
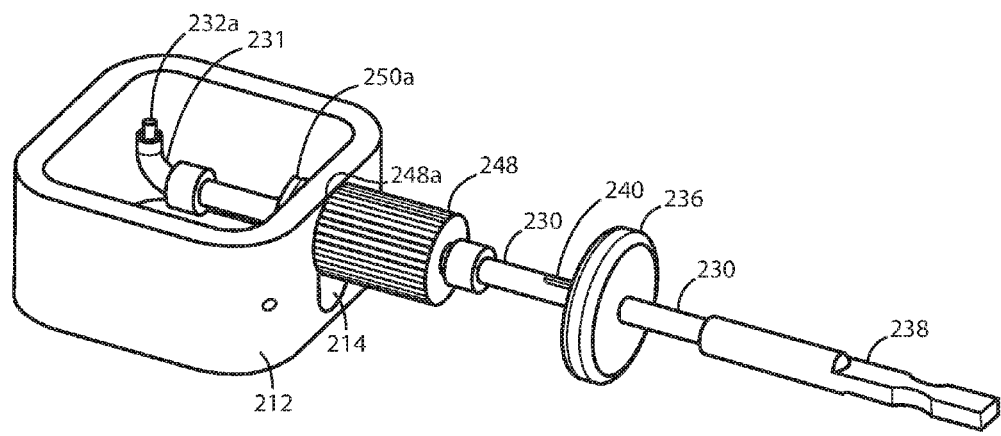
Figure 26:
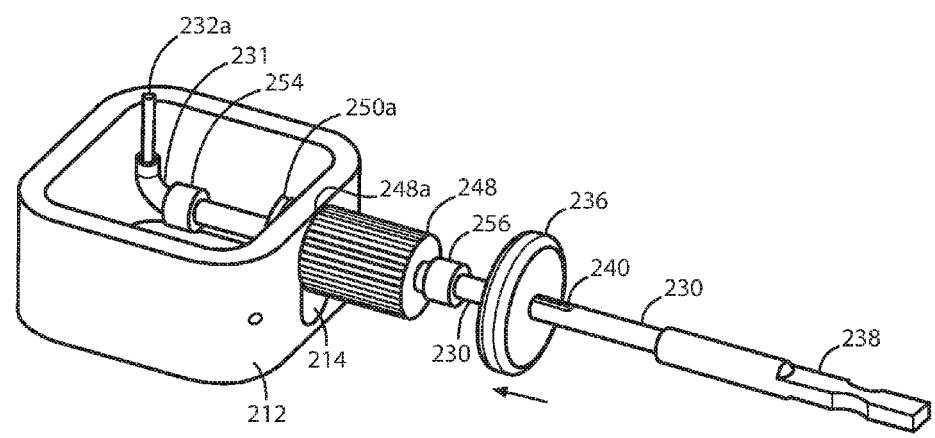
Figure 27:
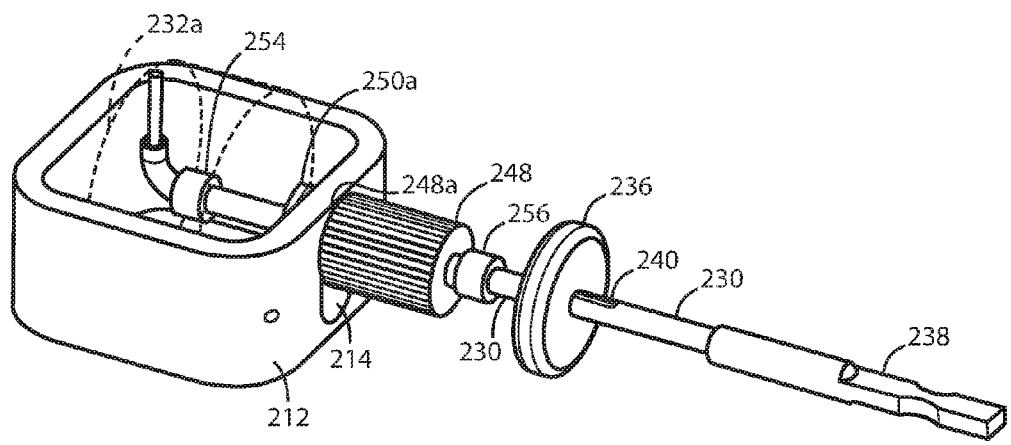
Figure 28:
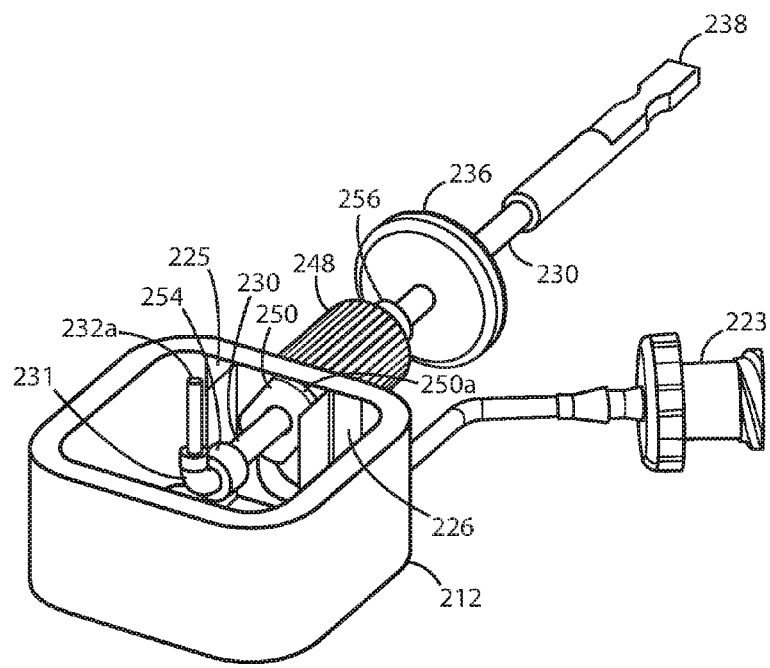
Figure 29:
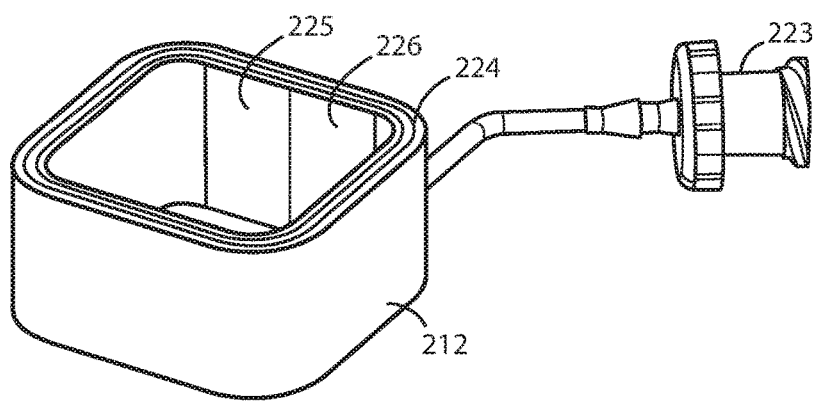
Figure 30:
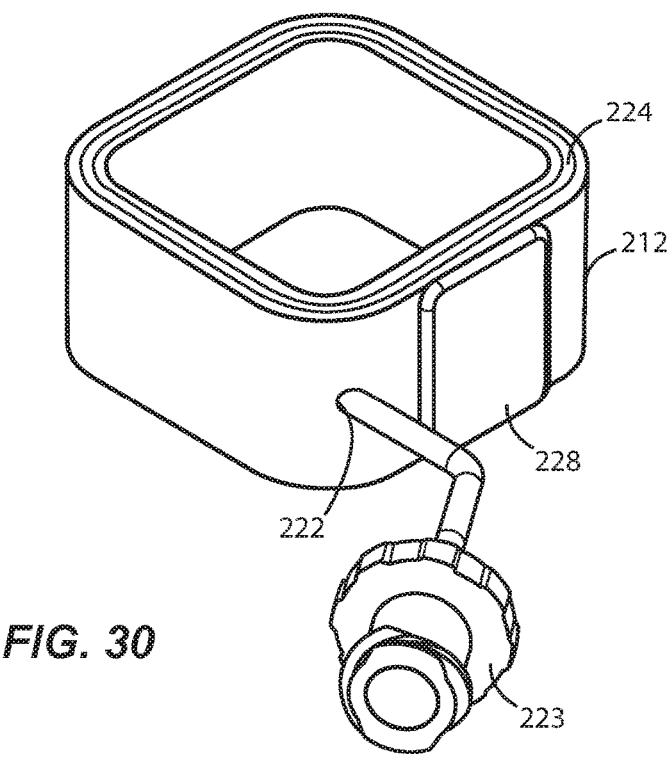
Figure 31:
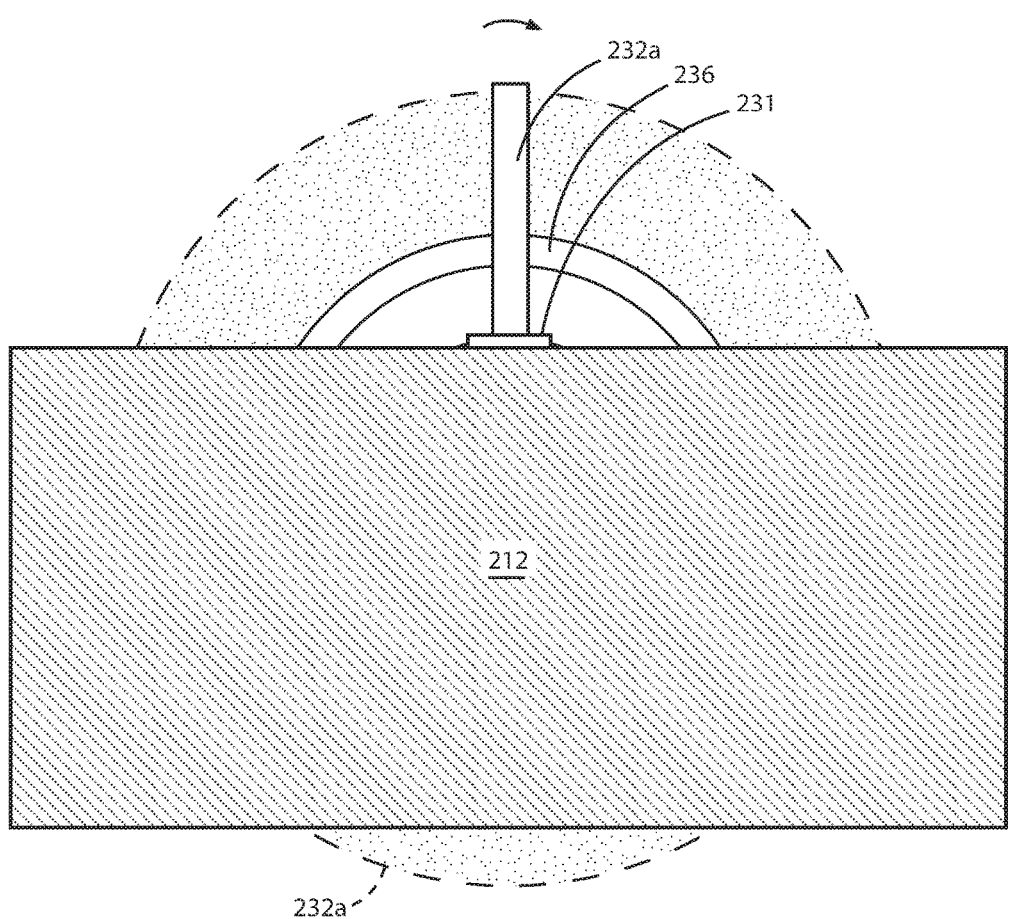
Figure 32:
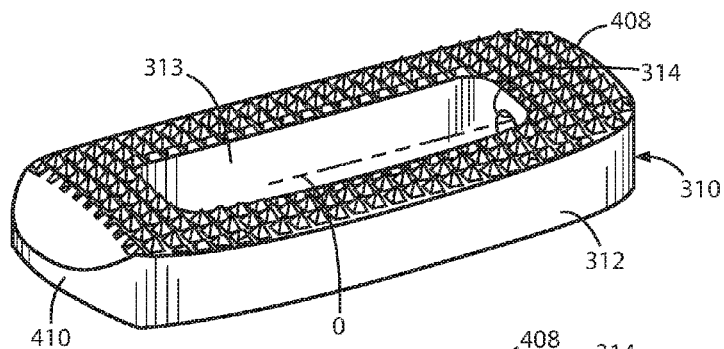
Figure 33:
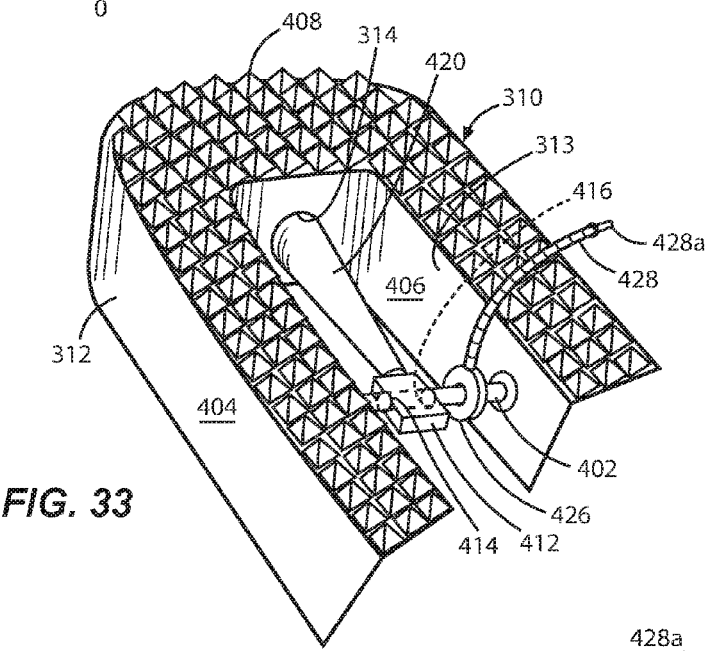
Figure 34:
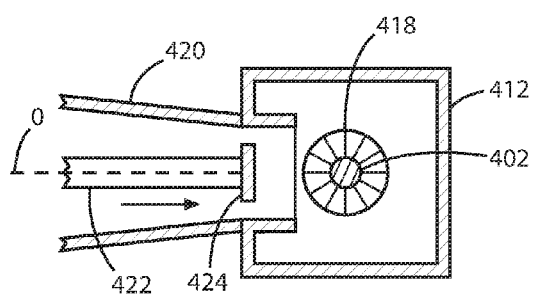
Figure 35:
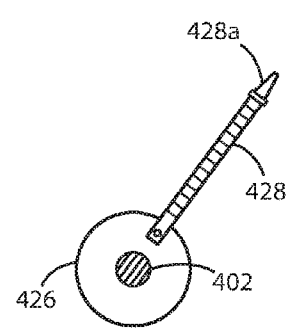

FIG. 9 shoes the bone segments in FIG. 6 acting as strut grafts between the vertebrae when the paddle is in the position in FIG. 8, according to the invention:

FIG. 10 shows the vertebrae in FIG. 1 before fusion and with a cage inserted in the disc space, according to another embodiment of the invention;

FIG. 11 shows a distal end of a cannula inserted in the disc space through an opening in a side wall of the cage in FIG. 10;

FIG. 12 shows a cutting tip of a flexible wire inserted through the cannula and into the disc space, with the wire tip angled toward one of the vertebrae;

FIG. 13 shows the tip of the wire cutting multiple grooves in the vertebrae to be fused;

FIG. 14 depicts the effusion of a bony slurry from the cut vertebrae, and the confinement of the slurry in the cage, according to the invention;

FIG. 15 shows the interior of a cage including a bone cutting blade and paddle mechanism fixed inside the cage, according to the invention;

FIG. 16 is an enlarged, isometric view of the blade and paddle mechanism in FIG. 15;

FIG. 17 is an isometric view of a housing of a cage device according to a further embodiment of the invention, showing a chamber inside the housing;

FIG. 18 is a view of the cage device housing as in FIG. 18, showing flaps inside the housing for sealing a slot opening formed in a side of the housing;

FIG. 19 is a view of a whip assembly according to the invention, including an elongated cannula and showing a cutting tip of a wire projecting from the cannula;

FIG. 20 is an enlarged view of a portion of the whip assembly in FIG. 19, showing internal parts of an advance knob of the assembly;

FIG. 21 is a view similar to FIG. 20 including the advance knob;

FIG. 22 is a view similar to FIG. 21 showing a center disk of the advance knob;

FIG. 23 is a view of the whip assembly in FIG. 19, with the advance knob at a retracted or initial position;

FIG. 24 is a view of the whip assembly as in FIG. 23, showing a distal end of the assembly entering the chamber in the device housing through the slot opening in the side of the housing;

FIG. 25 is a view of the whip assembly as in FIG. 24, with the distal end of the assembly set at a desired position inside the housing chamber;

FIG. 26 is a view of the whip assembly as in FIG. 25, with the advance knob set at an advanced position;

FIG. 27 is a view of the whip assembly as in FIG. 26, depicting a path of rotation of the wire cutting tip projecting from the cannula;

FIG. 28 shows the cage device housing as in FIG. 18, with the flaps parted for passage of the whip assembly through the slot opening, and a Luer fitting in fluid communication with internal passageways in the housing;

FIG. 29 shows the device housing as in FIG. 28, with the flaps closed after the whip assembly is withdrawn from the chamber;

FIG. 30 shows the device housing including an outside plug for sealing the slot opening after the whip assembly is withdrawn;

FIG. 31 is an enlarged, back end view of the cage device, depicting a path of rotation of the wire cutting tip above and below the device housing;

FIG. 32 is an isometric view of a cage or spacer device currently used in lateral lumbar interbody fusion (LLIF) surgery;

FIG. 33 is an enlarged partial view of the device in FIG. 32, including a bone cutting feature according to the invention;

FIG. 34 is an enlarged, sectional view through a gearbox inside the device in FIG. 33 according to the invention; and FIG. 35 is a side view, partly in section, showing a hub and bone cutting wire inside the device in FIG. 33 according to the invention.

DETAILED DESCRIPTION OF THE INVENTION

The present invention resides in a system for harvesting graft material directly from a patient during a surgical bone fusion procedure. In the illustrated embodiments, the procedure is a spinal fusion wherein the bones to be fused are vertebrae of the spine, and the harvested graft material is deposited to span a disc space between each pair of vertebrae to be fused. As a result, the material grows quickly to enter the vertebral bodies and obtain a healthy, solid, and permanent fusion. While the invention is described herein in terms of a spinal fusion, it will be understood that the invention may be applied to other fusion surgeries, for example, fusions of the ankle bones.

FIG. 1 is a diagram of two adjacent spinal vertebrae 10, 12. The spine has an axis S, and the vertebrae 10, 12 are separated by a disc space 14. End plates 10a, 12a on the vertebrae face one another across the disc space 14.

Figure 2:
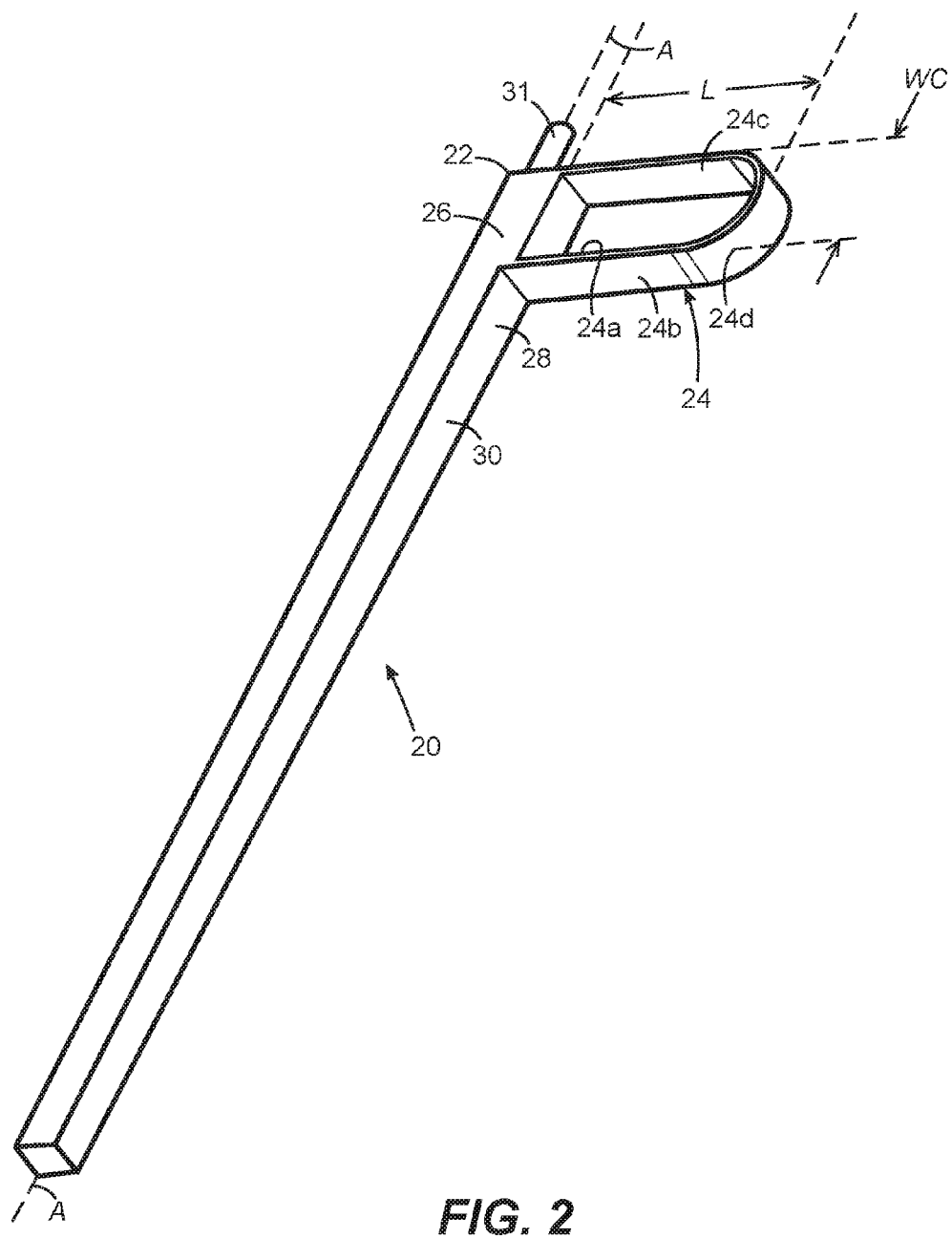
FIG. 2 shows a bone cutting tool having a shaft and a cutting blade at a distal end of the shaft, according to the invention.

In one embodiment of the invention, shown in FIGS. 2 to 9, a bone cutting tool has a shaft 30 with a long axis A, and a generally U-shaped, ultrasonic cutting blade 24. The blade 24 has a base 26, and a cutting edge 24a formed along parallel legs 24b, 24c and a closed end 24d of the U shaped blade 24. As shown in FIG. 2, the blade legs 24b, 24c are spaced apart by width WC, and the closed end 24d of the blade extends by a length L from the base 26.

Figure 3:
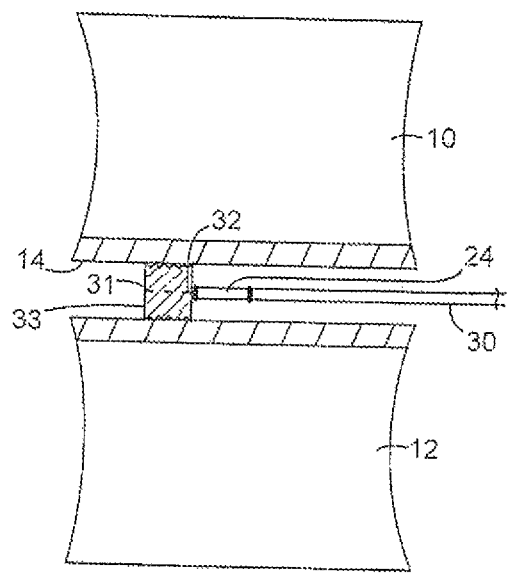
FIG. 3 shows the tool shaft in FIG. 2 inserted in a disc space between the vertebrae in FIG. 1, and a cage on which the shaft is pivoted to rotate with the blade.

The blade base 26 is formed by a distal end 28 of the tool shaft 30, and a pivot 31 projects axially from the distal end of the shaft. As seen in FIG. 3, the pivot 31 is received in a corresponding pivot opening 32 formed in a spacer or cage 33, after the cage 33 is fixed at a determined position in the disc space 14 between the vertebrae 10, 12. The cage 33 may be formed of a surgical metal, a polymer, a ceramic, or composites thereof. The pivot opening 32 in the cage 33 acts as an anchor point for the tool shaft 30 and any other instruments to be inserted in the disc space 14, while the cage 33 supports the vertebral bones 10, 12 above and below the disc space to prevent subsidence of bone graft segments to be obtained as described below. The cage 33 also serves to enhance the stability of the entire construct and thus ensure a successful fusion.

If surgery is performed using a posterior approach, the cage 33 is inserted in the disc space 14 from the posterior side, and should be urged anteriorly as far as possible to lodge against the disc annulus as the vertebral bones 10, 12 compress the cage 33 from above and below. To provide an effective anchor point for the pivot 31 on the tool shaft 30, the cage 33 should be relatively large and curvilinear in shape to conform with the anterior disc space occupied by the cage. Cages typically have one or more apertures to allow bone graft material to be deposited inside them, and for the material to be exposed to and contact the vertebrae above and below the cage to allow the material to grow and to bond the vertebrae 10, 12 solidly to one another.

Because, according to the invention, bone graft material is obtained directly from the vertebrae to be fused instead of an outside source, it is not necessary for the cage 33 to act primarily as a fusion device. That is, the cage 33 can work mainly as a fixation device that is joined to the vertebral bones 10, 12 above and below. An existing cage that also serves as a fixation device is available, for example, from Biomet, Inc., as the C-THRU™ Anterior Spinal System.

The Biomet cage has a large chamber that opens at the superior and inferior (top and bottom) ends of the cage, and in which graft material can be packed. Although as shown in FIG. 3 applicant's cage 33 is not centered directly with respect to the end plates 10a, 12a of the vertebrae to be fused, it may be desirable to use a cage similar to the Biomet cage which has a chamber that is open at both ends, and to form an opening in a side wall of the cage so that the entire blade 24 can be inserted into the cage chamber via the tool shaft 30. In such a case, the cage 33 could be centered on the vertebral end plates 10a, 12a before the blade 24 cuts into the end plates 10a, 12a, as described below. (See FIG. 11, and cage 100).

Figure 4:
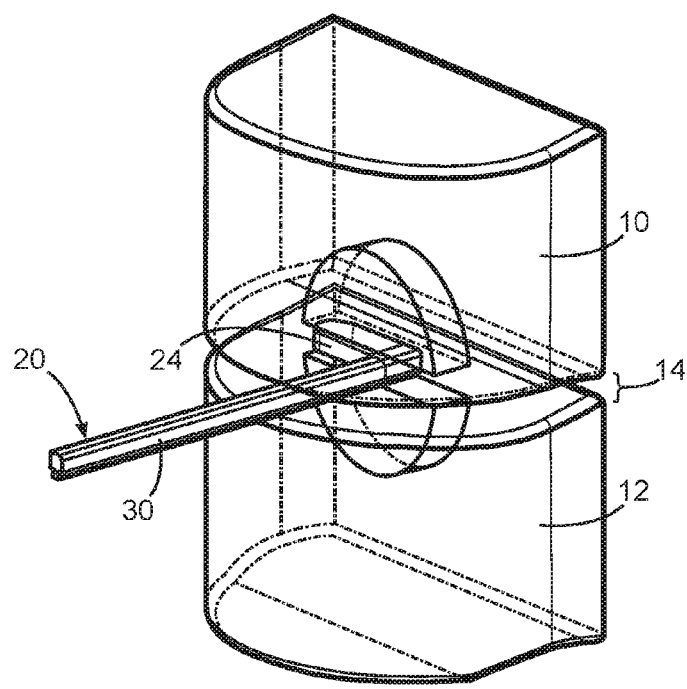
FIG. 4 is an enlarged, isometric view of the tool shaft and the blade inserted in the disc space as in FIG. 3.
Figure 5:
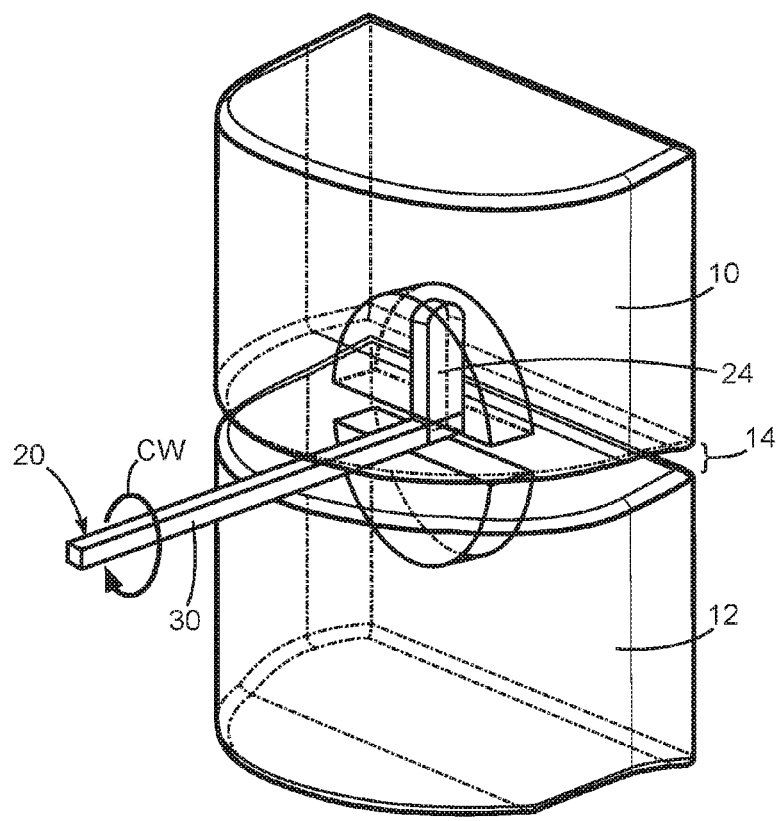
FIG. 5 is a view similar to FIG. 4, after the blade is turned 90 degrees from the position in FIG. 4 by the tool shaft.

As seen in FIG. 2, the U shaped blade 24 extends radially outward from base 26 at the distal end 28 of the tool shaft 30. The blade legs 24b, 24c and the closed end 24d of the blade 24 are in a plane that contains the shaft axis A. The bone cutting tool with the blade 24 is dimensioned and formed so that the blade 24 can be inserted by the tool shaft 30 to a desired position in the disc space 14, with the plane of the blade 24 kept generally parallel to the end plates 10a, 12a of the vertebrae to be fused as seen in FIG. 4. The cutting edge 24a along the blade 24 is activated, for example, by a conventional ultrasonic driver that is coupled in a known manner to the tool shaft 30. Ultrasonic bone cutting blades and methods of activating them are generally known, and persons of ordinary skill in the art should be able to construct and use the blade 24 as described herein. See, e.g., www.misonix.com.

The tool shaft 30 is rotated about its axis A by, e.g., a removable or cannulated handle having an axial thru passage keyed to the shaft cross section, or by a flexible motor drive, so that the blade's cutting edge 24a is urged a over a circular path through the vertebral end plates 10a, 12a, and included regions inside the vertebrae 10, 12. See FIG. 5. As a result and as illustrated in FIG. 6, the blade 24 forms two semi-circular solid bone segments 40, 42 in the vertebral bodies 10, 12, wherein the radius of each segment 40, 42 corresponds to the radial length L of the blade 24 and the thickness of each segment corresponds to the spacing WC between the parallel blade legs 24b, 24c.

The bone segments 40, 42 comprise autologous graft material that will form strut grafts between the same vertebrae 10, 12 from which the segments were cut, as described below. Note in FIG. 6 that after the segments are cut by the blade 24, relatively flat surfaces 40a, 42a on the segments are exposed to face one another across the intervertebral disc space 14. While the cutting blade 24 can be withdrawn from the disc space 14 at this time along with the tool shaft 30, it may be desirable to leave the blade 24 and shaft 30 in place, as noted below.

Figure 7:
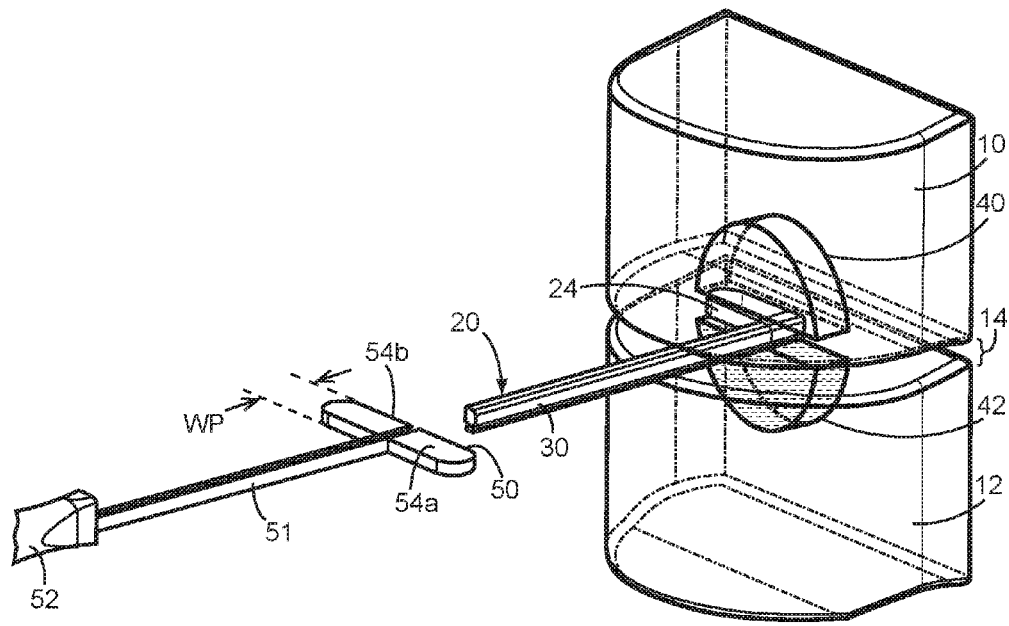
FIG. 7 is an isometric view of a pusher or paddle at a distal end of another shaft.

After removing a handle or other drive from the tool shaft 30, and as shown in FIGS. 7 to 9, an elongated pusher or paddle 50 is inserted into the disc space 14 until the paddle 50 is aligned with the blade 24 and the exposed surfaces of the bone segments 40, 42. In the illustrated embodiment, the paddle 50 is fixed at a distal end of a cannulated shaft 51 having an axial passage keyed to the cross section of the tool shaft 30. The cannulated shaft 51 is slid onto the tool shaft 30, a handle 52 is provided at the proximal end of the shaft 51, and the paddle 50 is inserted via the shaft 51 into the disc space 14. Using the handle 52, the paddle 50 (tog ether with the cutting blade 24 if left in place) is rotated about 90 degrees over the same circular path traversed by the blade 24 when forming the bone segments 40, 42, as described below.

If the cage 33 in FIG. 3 is of such size as to encompass areas of the vertebral end plates 10a, 12a to be cut by the blade 24, then both the blade 24 and paddle 50 should be able to be inserted and to operate inside the cage. In such a case, the cage 33 may be formed with passages in its anterior and posterior facing side walls, so that the passages allow the cutting blade 24, paddle 50, and other required instrumentation to enter the cage from either direction depending on the approach taken by the surgeon.

In the illustrated embodiment, the paddle 50 has two U shaped arms 54a, 54b that extend radially from the shaft 51 and 180 degrees apart from one another. See FIGS. 7 to 9. Each paddle arm 54a, 54b has a width WP that does not exceed the width WC of the bone cutting blade 24. Likewise, the length of each paddle arm 50a, 50b does not exceed about one-half the length of either of the bone segment surfaces 40a or 42a facing the disc space 14. The entire paddle 50 may also be formed from one or more balloons which, when inflated, take the form of a rigid pusher or paddle device.

When the paddle 50 is inserted in the disc space 14, the paddle arm s 54a, 54b are generally parallel to and overlie the surfaces 40a, 40b of the bone segments. The cannulated shaft 51 is turned about its axis A so that the paddle arms urge the bone segments 40, 42 confronting the arms to rotate partially out of the vertebra from which the segment was cut by, e.g., about 90 degrees as in FIG. 9. Accordingly, (i) a leading portion of each segment 40, 42 enters the vertebra opposite the vertebra from which the segment was cut, (ii) a central portion of each segment spans the disc space 14, and (iii) a trailing portion of each segment remains inside the vertebra from which it was cut.

When rotated as described above and shown in FIG. 9, each one of the bone segments 40, 42 forms a vertical strut graft that fully spans the disc space 14 and also penetrates both of the vertebrae 10, 12 to be fused. Each strut graft will therefore act as a pathway for bone growth and promote a healthy fusion of the two vertebrae. The tool shaft 30 may be withdrawn from the cage 33 inside the disc space 14, and the paddle 50 and the cutting blade 24 can remain in a vertical position sandwiched between the strut grafts formed by the bone segments with no adverse affect on the quality of the ensuing fusion.

After the blade 24 cuts into the vertebrae and the formed bone segments 40, 42 are rotated by the paddle 50, a massive release of blood is likely to occur since the bone is very vascular. Accordingly, in addition to inserting and using a cage similar to the mentioned Biomet device in the disc space 14, a system should be in place to extinguish such hemorraging. One approach is to use a coagulating agent such as, for example, the Surgiflo® Hemostatic Matrix available from Ethicon US, LLC, and injecting the agent through an applicator tube into a port formed on the cage 33. Also, with much bleeding, there may be a need to seal the disc space 14 so the coagulating agent will stay inside the space. That is, the disc space 14 may need to be capped or sealed closed to confine the blood, the coagulating agent, and the graft bone segments inside the disc space. Once the coagulating agent is injected in the closed disc space, a pressurized environment is created and bleeding should stop.

The cage may also have ports situated so that the coagulating agent produces a seal between the upper and the lower surfaces of the cage, and the adjacent vertebral bone. The seal should help to prevent bloody fluid from escaping above and below the cage through small gaps.

As the paddle 50 turns, and as described above, the paddle arms 54a, 54b are urged against the confronting surfaces 40a, 42a of the bone segments 40, 42 after the segments are cut and formed by the blade 24. The paddle 50 therefore does not occupy any space in which new bone graft will be deposited. Thus, as noted above, the paddle 50 can remain in the position in FIG. 9 with the graft bone segments 40, 42 at each side, and the vertebral bones 10, 12 above and below the paddle. Moreover, as the bones 10, 12 heal and the graft bone segments 40, 42 grow, the paddle 50 becomes firmly anchored inside the vertebrae 10, 12 and adds stability to the overall construct by pinning the vertebrae together. To that end, the paddle 50 may be constructed, for example, with extensible pins to engage the confronting surfaces 40a, 42a of the bone segments and/or the vertebrae 10, 12 above and below the paddle 50. Such engagement would stabilize the construct and ensure that the paddle 50 and the graft bone segments 40, 42 do not migrate. Together with the cage 33, the paddle 50 will also prevent subsidence from a collapse of the disc height.

It is also possible for the paddle 50 to be formed as a balloon so that, if desired after inflation and use, the paddle can be deflated and easily removed after being turned to the position in FIG. 9 along with the bone segments 40, 42 at either side. In such a scenario, any additional fixation that would otherwise result by using a more solid form of the paddle 50, would not be realized unless the balloons are later filled with a material such as, e.g., methyl methacrylate that would harden the balloons in place.

The paddle 50 may also be constructed in a known manner so that the paddle arms 54a, 54b overlie one another at one side of the cannulated shaft 51 as the paddle 50 is inserted in the disc space 14. Once positioned between the bone segments 40, 42, one of the paddle arms may then be displaced to the opposite side of the shaft 51 so that the paddle arms overlie the confronting surfaces 40a, 42a on both of the bone segments.

It may also be preferable to allow the solid bone cutting blade 24 to remain in situ, and no attempt made to withdraw it from between the bone segments 40, 42 once the bone segments are formed and the paddle 50 enters the disk space 14. This would help to ensure that the paddle arms 54a, 54b will follow the same path previously cut by the blade 24 when forming the bone segments. A deviation of even a millimeter to either side of the path might cause the paddle arms 54a, 54b to lock or jam against solid uncut vertebral bone and prevent the arms from urging the segments 40, 42 fully toward the position in FIG. 9. If the dimensional tolerances of the cage 33 allow enough precision with respect to positioning the cutting blade 24 and the paddle 50 during use, then it may be possible for the blade 24 to be withdrawn before the paddle 50 is inserted and the paddle arms are deployed.

The inventive system therefore has the following desirable features:

1. The bone cutting blade 24 can be activated ultrasonically to make the vertebral cuts safely and precisely;

2. The blade 24 and the paddle 50 can be made small enough to be inserted in the intervertebral disc space 14 during a minimally invasive surgical procedure; and 3. In addition to adding stability to the construct, the cage 33 provides a common fixed pivot point about which the cutting blade 24 and the paddle 50 can rotate, thereby ensuring that the bone segments 40, 42 will turn smoothly and accurately within the vertebrae 10, 12 when urged to do so by the paddle.

Another embodiment of the inventive system is illustrated in FIGS. 10 to 14. Instead of cutting and forming the solid graft bone segments 40, 42 and displacing the segments angularly as described above, a bone cutting instrument having a straight rather than a two-dimensional or U shaped cutting edge is inserted in the disc space 14. The instrument is operated so that the cutting edge strikes the vertebral bones 10, 12 and cuts grooves in the bones, whereupon a slurry of morselized cortical and cancellous bone rich in osteogenic cells and blood oozes from the grooved bones. By confining the slurry so that it fills the disc space 14, portions of the slurry will remain within the grooved portions of both vertebrae to achieve a solid bony fusion.

A cage 100 is set in the disc space between the vertebrae 10, 12. See FIG. 10. The cage 100 may be similar to the earlier mentioned Biomet C-THRU Anterior Spinal System device, or equivalent. In addition, the cage 100 should have sufficient size and volume to contain and confine the slurry obtained from the vertebrae as detailed below, and be constructed so that its edges seal any gaps between the cage and either bone 10, 12. Such sealing should prevent liquid graft material from migrating outside the internal chamber of the cage 100 and the intervertebral disc space. For example, a seal can be formed by constructing the cage 100 with internal and/or external channels that guide a sealing agent around the circumference of the superior and the inferior edges of the cage 100, and the agent can be injected into the cage during the fusion procedure. The mentioned Surgiflo® Hemostatic Matrix is an example of such a sealing agent.

As seen in FIGS. 11 to 13, a cannula 102 is inserted through an opening 104 in the wall of the cage 100, and a distal or leading end of the cannula 102 forms a tip 106 that is angled to face the vertebrae above and below the cage 100 when the cannula 102 is rotated about its axis. A flexible, strong wire having a cutting tip 108 is inserted axially through the cannula 102, so that the tip 108 projects past the angled tip 106 of the cannula by a sufficient distance to contact the end plates 10a, 12a of the vertebra as the cannula is rotated about its axis by an external drive mechanism. As a result, the cutting tip 108 of the wire will start to cut into the end plates 10a, 12a of both vertebrae.

By urging the wire farther into a proximal end of the cannula 102, the cutting tip 108 will cut grooves completely through the end plates and adjacent regions of the vertebrae 10, 12, as seen in FIG. 12. As the position of the wire cutting tip 108 with respect to the angled tip 106 of the cannula 102 is adjusted, the cannula may be moved axially in anterior and posterior directions so that the combined width WC of all the vertebral cuts can be increased as desired. See FIG. 13. When the cage 100 is sufficiently filled with slurry 110 obtained from the cut vertebrae, the cannula 102 and the wire cutting tip 108 are withdrawn together from inside the cage 100.

As a result and as shown in FIG. 14, all of the bony slurry 110 obtained from the cut vertebrae is contained either inside the cage 100 in the disc space, or within the vertebrae 10, 12 in the region of the grooved cuts. Upon healing, the slurry forms a solid bony fusion of the vertebrae. If needed, a second cage or other device can be provided to cap or otherwise seal the cage 100 and the disc space to ensure the slurry 110 stays confined before healing.

FIG. 15 is a plan view of the interior of a cage 120 having a built-in blade and paddle mechanism 122 constructed and arranged to be operated from outside the cage 120, according to a further embodiment of the invention. FIG. 16 is an enlarged, isometric view of the blade and paddle mechanism 122.

The cage 120 may be formed, for example, from a surgically approved metal or metal alloy, or a strong plastics such as polyether ether ketone (PEEK). The side walls of the cage 120 as viewed in FIG. 15 are preferably as thin as possible while still having enough strength to prevent the cage 120 from deforming after the cage is inserted and fixed between spinal vertebrae or other bones to be fused.

A front wall 123 of the cage 120 in FIG. 15 has an opening 125 in which a head 126 of a first shaft 130 and a front end of a second shaft 140 (see FIG. 16) can each be accessed by a corresponding tool to rotate the associated shaft. That is, the shafts 130, 140 can be rotated independently of one another as desired by a mating tool from outside the cage 120. In the disclosed embodiment, the first shaft 130 is hollow, and the second shaft 140 extends coaxially inside the first shaft 130.

As shown in FIG. 16, the head 126 of the first (or outer) shaft 130 is, for example, in the form of a cylindrical socket having a series of teeth or grooves formed about its inner circumference for engaging a mating tool bit. The outer shaft 130 extends axially a certain distance from a rear wall 132 of head 126 toward a back wall of the cage 120, and a first leg 124b of a generally U-shaped bone cutting blade 124, which may be similar to the blade 24 in FIG. 2, is joined at one end of the leg 124b to the shaft 130. The second leg 124c of the blade 124 is joined to a front end of a sleeve 136 that is aligned axially with the outer shaft 130, and a rear end of the sleeve 136 is seated in the rear wall of the cage 120 at 138 (FIG. 15) for smooth rotation about the sleeve axis.

The second (or inner) shaft 140 of the blade and paddle mechanism 122 extends axially inside the outer shaft 130, and through the sleeve 136 toward the rear of the cage 120. The front end of the inner shaft 140 is keyed and is accessible within the cylindrical head 126 of the outer shaft 130 so that the front end of the shaft can be engaged for rotation by a mating tool bit. A section of the inner shaft 140 is exposed between the end of the outer shaft 130 to which the blade leg 124b is joined, and the front end of the sleeve 136 to which the blade leg 124c is joined.

A paddle 150 has a pair of arms 150a, 150b that extend radially from either side of the exposed section of the inner shaft 140, and the arms are spaced 180 degrees apart from one another. The paddle arms 150a, 150b are dimensioned and arranged to displace solid bone segments that are formed inside the bones to be fused after the blade 124 is rotated to cut into the bones, to positions at which the bone segments span and enter the bones to form strut grafts. The axial width and the radial length of the paddle arms 150a, 150b are such that when the U-shaped blade 124 is rotated by the outer shaft 130 over one full revolution while the paddle arms remain stationary, the blade 124 clears the perimeters of the paddle arms by at least 1 mm, and preferably by not more than 5 mm.

In use, and as in the first embodiment of the present invention, the blade 124 is activated and rotated 360 degrees by the outer shaft 130 so as to cut into the bones above and below the cage 120 and thus form two semicircular solid bone segments. After the segments are formed, the paddle arms 150a, 150b are displaced angularly about 90 degrees by the inner shaft 140. Each bone segment is thereby urged by a confronting paddle arm to rotate until (i) a leading portion of the segment enters the opposed bone, (ii) a central portion of the segment spans the space in which the cage 120 is fixed between the bones, and (iii) a trailing portion of the segment remains in the bone in which it was formed.

It will be understood that while the invention is described herein as applied to a spinal fusion, it may be adapted for other bone fusion procedures as well, for example, fusions of the ankle bones. Further, although a particular configuration is disclosed to enable the blade and paddle shafts 130, 140 to be turned as desired from outside the cage 120, other equivalent configurations for rotating the blade 124 and the paddle 150 inside the cage may also be used. See, e.g., U.S. Pat. No. 7,972,364 (Jul. 5, 2011) which is incorporated by reference.

FIGS. 17 to 31 to show components of a cage device 210 for bone fusion surgery according to a further embodiment of the invention. Like the cage 100 described herein, the cage device 210 is constructed and arranged to be used, for example, in a spinal bone fusion procedure by inserting and positioning the device within a disc space between two vertebrae to be fused, and operating the device to cut grooves into the end plates and adjacent regions of the vertebra. As a result, a slurry of morselized cortical and cancellous bone rich in osteogenic cells and blood oozes from the grooved end plates, and the slurry is received and confined inside a chamber of the device in which the slurry is allowed to grow and produce a solid bony fusion of the vertebrae.

In the illustrated embodiment, the cage device 210 is comprised of a generally square or rectangular cylindrical housing or wall 212 that measures, for example and without limitation, between 8 mm and 12 mm in height. Alternatively, the perimeter of the wall 212 may be generally circular, elliptical, or other shape to suit a given application.

The wall 212 of the cage device 210 has an elongated slot 214 that extends between a superior or upper edge 216, and an inferior or lower edge 218 of the wall. The slot 214 is formed and dimensioned to allow a leading portion of a bone cutter assembly 220 shown in FIGS. 19 to 23 (hereafter called a "whip" assembly) to pass through the slot 214 after the cage device 210 is fixed in a disc space between two vertebrae to be fused. The slot 214 is elongated so that the position of the whip assembly 220 can be adjusted either up or down relative to the device wall 212 in order to cut a desired depth into the vertebrae as explained below.

The device wall 212 forms an internal chamber 213 of the cage device 210. The chamber 213 is of a sufficient size to contain the expected volume of slurry, and the wall 212 is formed to allow any gaps between the edges 216, 218 of the wall and the vertebral end plates to be sealed. Such sealing is necessary to prevent the slurry from escaping the cage device 210 and to confine the slurry within the disc space in which the device is inserted.

Preferably, a coagulant lumen port 222 is formed in the device wall 212 for allowing a liquid sealing agent (e.g., Surgiflo Hemostatic Matrix) to be communicated via, e.g., a Luer™ fitting 223 (see FIGS. 29 and 30) into a trough or recessed channel 224 formed continuously in the upper and the lower wall edges 216, 218. Each channel 224 may be, e.g., about one mm deep and two mm wide. The sealing agent can enter and fill each channel 224 through a passage formed within the device wall 212 between the lumen port 222 and the channel. In addition, if a porous coating like titanium is provided on each edge, the sealing agent will permeate and be expressed through the coating.

Cages are often made from polyether ether ketone (PEEK) and have a porous titanium coating on the upper and lower edges the cage. Because PEEK is hydrophobic, and bone prefers to grow into a rough surface like titanium, a plasma layer would grow between the PEEK material and the bone in the absence of the titanium coating. Thus, by infusing a coagulant directly into a porous coating on the edges 216, 218 of the device wall 212, the growth of bone into the edges will be enhanced.

The direction of bone growth is from each vertebral end plate toward the adjoining edge of the cage device wall 212. By having any gaps between each edge filled in situ with a bone growth and sealing material, a greater chance of success for fusion is created. Because bone growth and sealing materials may be injected into the cage device 210 while the device is in place, an intimate bond between the vertebral bones will be created. As far as is known, no surgical device is available that allows this kind of material placement to occur.

It will also be understood that instead of forming a channel 224 in each edge 216, 218 of the device wall 212, and a passage between each channel and the lumen port 222, multiple passages leading from the port 222 may be formed within the wall 212 which open along each edge. Further, to promote growth and solidification of bone and blood slurry contained in the device chamber 213, another passage can lead from the lumen port 222, or a second port, to open directly into the device chamber 213, thus allowing a coagulant to be delivered directly into the contained slurry.

As shown in FIG. 18, one or more sealing elements or flaps 225, 226 are provided on the chamber side of the device wall 212. The flaps 225, 226 are configured to (a) seal the elongated slot 214 while the whip assembly 220 is fully withdrawn from the chamber 213, and (b) move clear of the slot 214 when a leading portion of the whip assembly 220 is inserted into the chamber 213 through the slot 214. When in the seal position (a), the flaps 225, 226 prevent bone fragments, blood, and/or coagulant contained in the chamber 213 from escaping through the slot 214. Alternatively, as shown in FIG. 30, a plug 228 may be inserted in the slot 214 from outside the device wall 212 to prevent any slurry contained in the chamber 213 from escaping.

As seen in FIGS. 19 to 23, the whip assembly 220 is comprised of an elongated cannula 230 having a passage along its axis A. The cannula 230 is made of stainless steel or an equivalent material suited and approved for surgical use, and forms a bend of, e.g., 90 degrees or less at a distal end or tip 231 of the cannula. A strong flexible wire 232 is inserted through the cannula passage over a leading portion 234 of the whip assembly 220, so that a cutting tip 232a of the wire extends out of the passage at the distal end 231 of the cannula.

As shown in FIGS. 20 to 22, a circular knob 236 is mounted coaxially on the cannula 230, and the knob is arranged to slide over an elongated axial slot 240 in the wall of the cannula. A proximal end 232b of the wire 232 in the cannula passage is bent to project radially through the slot 240, and the wire end 232b is captured in a center disk 242 of the knob 236. Thus, when the knob 236 is moved to the end of the slot 240 closer to the distal end 231 of the cannula 230 as in FIGS. 20 to 22, the cutting tip 232a of the wire 232 projects a greatest distance from the distal end 231 of the cannula as in FIG. 19. When the knob 236 is moved to the end of the slot 240 farthest from the distal end of the cannula as in FIGS. 23 to 25, the wire cutting tip 232a projects a least distance from the distal end 231 of the cannula.

Knob 236 has an outer ring 244 attached to the circumference of the center disk 242 of the knob, such that the disk 242 can rotate freely with respect to the ring 244 while the ring is manually held at a fixed position. Thus, when the cannula 230 and the center disk 242 of the knob 236 are rotationally driven about their axis A as explained below, the knob 236 can be urged to move in either direction over the slot 240 in the cannula by grasping and applying a corresponding force to the outer ring 244 of the knob.

As shown in FIGS. 23 to 28, a drive shaft 238 is joined axially to the cannula 230 at a proximal end of the whip assembly 220. The shaft 238 is dimensioned and configured to be engaged by a drill or other rotational drive via a chuck, collet, or other coupling mechanism. Accordingly, when (i) the leading end of the whip assembly 220 is inserted in the chamber 213 of the cage device 220 through the slot 214 in the device wall 212, (ii) the wire cutting tip is set via the knob 236 to extend a certain distance from the leading end of the cannula, and (iii) the shaft 238 is rotationally driven, the leading end 231 of the cannula 230 sweeps or "whips"

the wire cutting tip 232a over the end plates of the vertebrae facing the edges 216, 218 of the device wall 212. See FIGS. 27 and 31.

The whip assembly 220 also includes a cylindrical knob 248, and a retaining collar 250 that is joined axially to an end face 248a of the knob 248 closer to the distal end 231 of the cannula 230. The knob 248 with collar 250 are mounted coaxially for relative sliding movement over the cannula. The outside surface of the knob 248 may be knurled or grooved as shown to facilitate grasping and turning the knob 248 with the collar 250 by hand. The collar 250 has a pair of diametrically opposed, radially extending ears 250a, 250b dimensioned to clear the elongated slot 214 in the device wall 212 when the ears are aligned in the direction of the slot, and the distal end 231 of the cannula is inserted through the slot to enter the device chamber 213.

Once the distal end 231 of the cannula 230 is inserted through the wall slot 214 and enters the device chamber 213, the knob 248 is turned by about, e.g., 45 degrees to a position where the collar ears 250a, 250b engage the inside surface of the device wall 212 by friction in order to support the whip assembly 220 for operation. When desired, the surgeon can turn the knob 248 to realign the collar ears 250a, 250b with the slot 214, slide the whip assembly 220 up or down in the slot to place the distal end 231 of the cannula at a different vertical position inside the device chamber 213, and turn the knob again to support the whip assembly for operation. See FIGS. 24 to 27.

The whip assembly 220 also has two stop rings 254, 256 mounted coaxially on the cannula 230 for limiting the distance over which the distal end 231 of the cannula 230 can move in the axial direction inside the device chamber 213. By adjusting the axial positions of the two rings 254, 256 over the length of the cannula, the surgeon can define the location and the overall width of a series of cuts to be made by the wire cutting tip 232a into bone above and below the cage device 210. The depth of the cuts is determined by the radial distance the wire cutting tip 232a extends from the distal end 231 of the cannula, and the vertical position at which the whip assembly 220 is supported in the slot 214 in the device wall 212.

Prior to closing the surgical site and after a determined series of grooves are cut by the wire cutting tip 232a, the cannula 230 is withdrawn from the chamber 213 of the device 210 by turning the knob 248 to align the collar ears 250a, 250b with the wall slot 214. The sealing flaps 225, 226, or the chamber plug 228, then work to ensure that slurry contained the device chamber 213 remains in the patient's body after the surgical site is closed.

Bone healing may also be enhanced if a substance other than a common coagulant is injected through the lumen port 222. For example, surgeons now use stem cells derived from a patient's bone marrow or produced commercially to enhance bone fusion. A liquid containing these cells or other bone growth enhancing cells may be mixed with the coagulant or used alone.

Moreover, it may be possible for the whip assembly 220 to be used as a stand alone tool for surgery. That is, the cage device wall 212 as described and illustrated herein may not always be needed in order for the assembly 220 to work. For example, when performing a spinal fusion procedure from the back of a patient, a surgeon may first insert a small cage into the disc space, fully anterior. The leading portion 234 of the assembly 220 could be adapted to be supported by the posterior aspect of the cage, and the defect in bone above and below made by operating the assembly 220. While such a procedure would not address or contain any resultant bleeding, other suitable methods of controlling bleeding may be applied or developed.

FIG. 32 shows an existing cage or spacer device 310 that is dimensioned and configured for lateral lumbar interbody fusion (LLIF). The device 310 is commercially available and may be obtained from, e.g., Globus Medical, Inc., under the mark TransContinental®. Device 310 has a generally rectangular body comprised of an outer wall 312 that forms a relatively narrow chamber 313 within the device. See U.S. Pat. No. D625,820 (Oct. 19, 2010) and D629,104 (Dec. 14, 2010), both of which are incorporated by reference. During surgery, the device 310 is inserted laterally in the disc space between two vertebrae to be fused by use of an inserter tool that engages an opening 314 formed in a short side of the wall 312.

If the distal end of the whip assembly 220 in FIG. 19 is passed into the chamber 313 of the device 310 through opening 314 after the device is inserted between vertebrae, the distance over which the wire cutting tip 232a of the assembly can be extended is limited by the relatively narrow spacing between the long sides of the device wall 312. That is, when driven to rotate about the axis of the assembly 220, the wire cutting tip 232a will strike against the long sides of the wall 312 inside the chamber 313 before the tip can be extended far enough to cut the adjacent vertebrae.

FIGS. 33 to 35 show an improvement of the cage or spacer device 310 in FIG. 32 that allows a wire cutting tip to rotate and cut grooves into bone above and below the device chamber 313, according to the invention. A round shaft 402 is supported to extend between the long sides 404, 406 of the device wall 312 inside the chamber 313, substantially midway between the short sides 408, 410 of the wall. The shaft 402 is mounted for rotation about its axis, for example, by supporting the opposite ends of the shaft within sleeve bearings embedded in the long sides 404, 406 of the wall 312. In the illustrated embodiment, the shaft 402 lies substantially in a plane that contains the axis O of the opening 314 in the short side 408 of the wall.

A gearbox 412 is disposed on the shaft 402 at a position substantially midway between the long sides 404, 406 of the wall 312, and the shaft 402 is passed for rotation through sleeve bearings 414, 416 that are fixed in opposite sides of the gearbox 412. A first bevel gear 418 is fixed coaxially on the shaft 402 inside the gearbox 412, and a side of the gearbox facing the short side 408 of the wall 312 is open to allow access to the bevel gear 418.

One end of a sleeve 420 is fixed in alignment with the axis O of the opening 314 in the short side 408 of the device wall 312. The opposite end of the sleeve 420 is fixed to the side of the gearbox 412 that is open to access the bevel gear 418. Accordingly, when a flexible or rigid rotating drive 422 having a second bevel gear 424 at a distal end of the drive is inserted through the opening 314 in the device wall, the drive 422 passes inside the sleeve 420 until the second bevel gear 424 at the end of the drive engages the first bevel gear 418 fixed on the shaft 402. When the drive 422 is rotationally driven by a motor or other component outside the cage device 310, the engaged bevel gears 418, 424 drive the shaft 402 inside the device to turn about an axis that is offset by substantially 90 degrees from the axis O of the opening 314 in the device wall.

One or more hubs 426 are fixed coaxially on the shaft 402 at positions outside the gearbox 412. One or more wires 428 each having a cutting tip 428a at a distal end of the wire are fixed to each hub 426. The wires 428 should be flexible enough so they can be contained within the device chamber 313 when the cage device 310 is inserted between adjacent vertebrae or other bones to be fused. Because the plane of rotation of the wires 428 on each hub is parallel to the long sides 404, 406 of the device wall 312, the length of the wires 428 is not limited by the relatively narrow width of the device chamber 313. Thus, when the shaft 402 inside the cage device 310 is driven to rotate, the cutting tips 428a on the wires 428 can extend above and below the cage device 310 by an amount sufficient to cut into and groove the surfaces of bones between which the device 310 is inserted.

Further, if a metal rod is used for the rotating drive 422, the same rod may be used to insert the cage device 310 itself if, for example, the drive 422 is initially surrounded by a removable metal outer tube a distal end of which is formed to engage the opening 314 in the short side 408 of the cage device 310. The surgeon can then use a mallet to hammer on a proximal end of the drive 422 and surrounding tube, and thus urge the cage device 310 into a disc space. Once the device is inserted, the surrounding tube is removed from the drive 422 so that the drive is free to rotate.

While certain embodiments of the invention are disclosed herein, it will be understood by those skilled in the art that various modifications, adaptations, and additions may be made without departing from the spirit and scope of the invention. For example, while bevel gears 418, 424 are disclosed for enabling the shaft 402 inside the inventive device to be rotationally driven about an axis that is offset 90 degrees from the axis O of the opening 314 in the device wall 312, it will be understood that equivalent mechanisms, e.g., worm gear drives, can be used instead. Accordingly, the invention includes all such modifications, adaptations, and additions as are within the scope of the following claims.

I claim:

1. A bone cutter assembly for harvesting bone graft material for use in fusion surgery, comprising:
    an elongated cannula extending from a proximal end to a distal end along a longitudinal axis, said elongated cannula having a bend formed at the distal end or a distal tip of the cannula, and having a through bore extending along said longitudinal axis through said proximal end and said distal tip of the cannula, wherein the cannula is constructed and arranged to be supported at inserted to a desired position in a space between bones to be fused; and
    an elongated wire having a cutting distal tip, wherein the wire is inserted through the through bore of the cannula so that the cutting distal tip is configured to extend a desired distance distally beyond the distal tip of the elongated cannula for contacting the bones to be fused, and the cutting tip is operative to cut grooves in the bones when the cannula is rotated about its axis by an outside drive so that a slurry of morselized bone and blood effuses from the grooved bones to promote fusion of the bones;
    the cannula has an elongated side slot opens the through bore into an outside of the elongated cannula and a proximal end of the wire in the cannula is bent to project radially through the slot, and including a first proximal knob mounted coaxially on the cannula for sliding movement over the slot, wherein the proximal end of the wire is captured by the first knob so that the cutting tip of the wire is configured to be set to extend a desired distance from the distal end of the cannula according to the position of the first knob over the slot;
    a second distal knob mounted coaxially for sliding movement over the elongated cannula and for rotation about the longitudinal axis relative to the cannula, wherein the second distal knob comprises a retaining collar mounted coaxially over the elongated cannula and having radially extending ears configured to engage by friction a fixed surface of a device in the region of the bones to be fused for supporting the cannula at the desired position in the space between the bones;
    two stop rings mounted coaxially on a distal portion of the elongated cannula and at corresponding distal and proximal sides of the second distal knob, for limiting the axial sliding of the elongated cannula relative to the second distal knob when the distal end is inserted into the space between the bones to be fused and the retaining collar is engaged to the fixed surface, so that a surgeon can define the location and the overall width of a series of cuts to be made by the cutting tip of the wire into bone above and below the distal end of the cannula by adjusting the axial positions of the stop rings over the length of the cannula at the sides of the second knob; and
    wherein the axial sliding of the second distal knob along the elongated cannula causes the retaining collar to slide axially along the elongated cannula, and the rotation of the second distal knob about the longitudinal axis relative to the elongated cannula causes the retaining collar to rotate about the longitudinal axis relative to the elongated cannula.

2. A bone cutter assembly according to claim 1, including a drive shaft joined axially to the cannula at the proximal end of the cannula, and the shaft is arranged to be driven by a rotational drive so that when the cannula is inserted in the in the space between the bones to be fused and the wire cutting tip extends the desired distance from the cannula, the tip cuts into and grooves the surfaces of the bones.

3. A bone cutter assembly according to claim 1, wherein the first proximal knob includes a center disk in which the bent proximal end of the wire is captured, and an outer ring is attached to the circumference of the center disk so that the disk rotates freely with respect to the ring when the ring is held at a fixed position and the cannula is rotated about its axis.

* * * * *